(12) United States Patent
Salmon et al.

(10) Patent No.: US 6,719,780 B1
(45) Date of Patent: *Apr. 13, 2004

(54) WARMING METHODS AND APPARATUS

(75) Inventors: Andrew Paul Maxwell Salmon, Auckland (NZ); Roger Conway, Auckland (NZ)

(73) Assignee: Fisher & Paykel Limited, Auckland (NZ)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/662,109

(22) Filed: Sep. 14, 2000

(30) Foreign Application Priority Data

Sep. 21, 1999 (NZ) .............................. 337949
Nov. 23, 1999 (NZ) .............................. 501245

(51) Int. Cl.[7] .................................. A61F 7/00
(52) U.S. Cl. ...................... 607/108; 607/109
(58) Field of Search ............... 607/108, 112, 607/96, 91, 90, 88, 100, 109

(56) References Cited

U.S. PATENT DOCUMENTS

| | | | | |
|---|---|---|---|---|
| 3,789,853 A | * | 2/1974 | Reinhard | 392/411 |
| 4,658,823 A | * | 4/1987 | Beddoe et al. | 607/90 |
| 4,832,029 A | * | 5/1989 | Koch et al. | 362/130 |
| 4,969,459 A | * | 11/1990 | Gusakov | 128/905 |
| 5,649,972 A | * | 7/1997 | Hochstein | 219/531 |
| 5,683,438 A | | 11/1997 | Grahn | |
| 5,830,123 A | * | 11/1998 | Franz et al. | 600/22 |
| 6,317,636 B1 | * | 11/2001 | Fujii | 607/100 |
| 6,327,506 B1 | * | 12/2001 | Yogo et al. | 128/898 |

FOREIGN PATENT DOCUMENTS

| | | |
|---|---|---|
| EP | 1086673 | 3/2001 |
| JP | 1112819 | 1/1999 |
| WO | WO9428834 | 12/1994 |
| WO | WO9840039 | 9/1998 |
| WO | WO9923980 | 5/1999 |
| WO | WO0158396 | 8/2001 |
| WO | WO0200146 | 1/2002 |

* cited by examiner

Primary Examiner—Michael Peffley

(57) ABSTRACT

Apparatus and method for raising or maintaining the core temperature of a mammal during surgery is disclosed. The apparatus comprises a infrared radiant element with a double reflector design to provide a very narrow beam of radiation. In this fashion the apparatus is able to direct radiant energy at the mammal's skin in regions with a high concentration of Arteriovenous Anastomoses. The apparatus also includes a skin temperature sensor to allow closed loop control of the heat energy supplied to the mammal. The complete apparatus can be located in an unobtrusive position such that it does not interfere with the surgical team.

14 Claims, 4 Drawing Sheets

WARMING METHODS AND APPARATUS

BACKGROUND TO THE INVENTION i) Field of the Invention

This invention relates to apparatus and methods of patient warming and in particular to apparatus and methods for maintaining or restoring intra-operative normothermia.

ii) Summary of the Prior Art

Many methods of warming patients during surgery are known in the art. For example, the air conditioning system in the operating theatre may be adjusted to suit the temperature needs of the patient. However, in this case, the surgical team may suffer ill-effects from overheating. Further, this method may also not provide enough heating for the patient.

If extra heating is required, additional convection heating can be used to directly heat the patient. However, as well as being inefficient and in some cases ineffective, additional heating apparatus is likely to be bulky and may impair the surgical team's ability to perform the surgery.

SUMMARY OF THE INVENTION

It is an object of the present invention to provide an apparatus or method of warming a patient which goes some way to overcoming the abovementioned disadvantages or which will at least provide the healthcare industry with a useful choice.

Accordingly in a first aspect the present invention consists in a method of raising or maintaining the core temperature of a mammal using a radiant heater comprising or including the steps of:

1) positioning the radiant heater in a non-obtrusive manner in proximity to said mammal;
2) energising said radiant heater;
3) directing the radiant energy produced in step (2) at said mammal, substantially at a region of the skin of said mammal with a high concentration of Arteriovenous Anastomoses; and
4) controlling the energisation of said radiant heater such that said mammal's skin temperature remains within a predetermined range.

In a second aspect the invention consists in an apparatus for raising or maintaining the core temperature of a mammal comprising:

radiant heating means which in use are located in an unobtrusive position proximate to said mammal, means adapted to direct radiant energy produced by said radiant heating means at said mammal, substantially at a region of the skin of said mammal with a high concentration of Arteriovenous Anastomoses, and control means which energise said radiant heatng means such that in use said mammal's skin temperature remains within a predetermined range.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DETAILED DESCRIPTION

The present invention is particularly useful for the maintenance of intra-operative normothermia and treatment of hypothermia in surgical patients. Due to space limitations in the surgical area, the traditional heating area of the thoracic region is inaccessible in some circumstances.

The present invention overcomes this by heating the patient in the head/neck area using infra red heating techniques.

It has been found that, despite this small area, the use of the present invention is effective in not only maintaining normothermia, but also in restoring normothermia in those patients who had become hypothermic, by achieving a net heat gain in the patient. In some patients, due to the type of surgical procedure or logistical constraints, it might be very difficult or impossible to effectively treat them via conventional means, i.e. the use of a convective air warmer.

Figure 1:
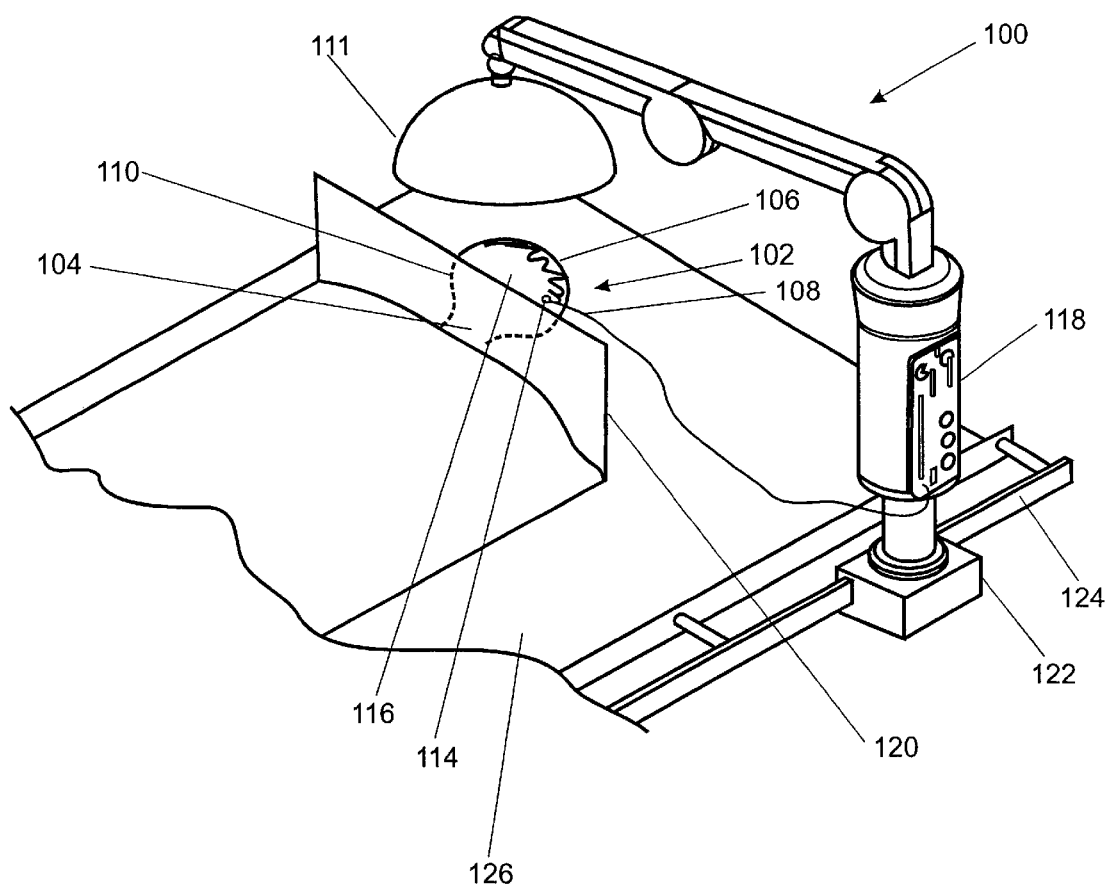
FIG. 1 is a block diagram of the present invention in use heating the head and neck region.

In the preferred embodiment of the present invention seen in FIG. 1, the unit 100 is positioned over the patient's head/neck area 102 with the edges of the IR beam being the base of the neck 104 to the top of the head 106 and outside of each ear 108, 110. With only a small surface area to work with, the distance between the warmer head 111 and the patient 112 is 20–50 cm, to ensure effective intensity of the IR. A skin sensor 114 is positioned on the most prominent point on the patient's face 116, (forehead or chin if the patient's head is upright, or on their cheek if head turned to the side). Alternatively a non contact sensor may be used, as all that is required is some estimate of either the energy absorbed by the patient or the skin temperature of the patient. A surgical drape 120 may be used to shield the surgical team from any stray radiation.

Figure 3:
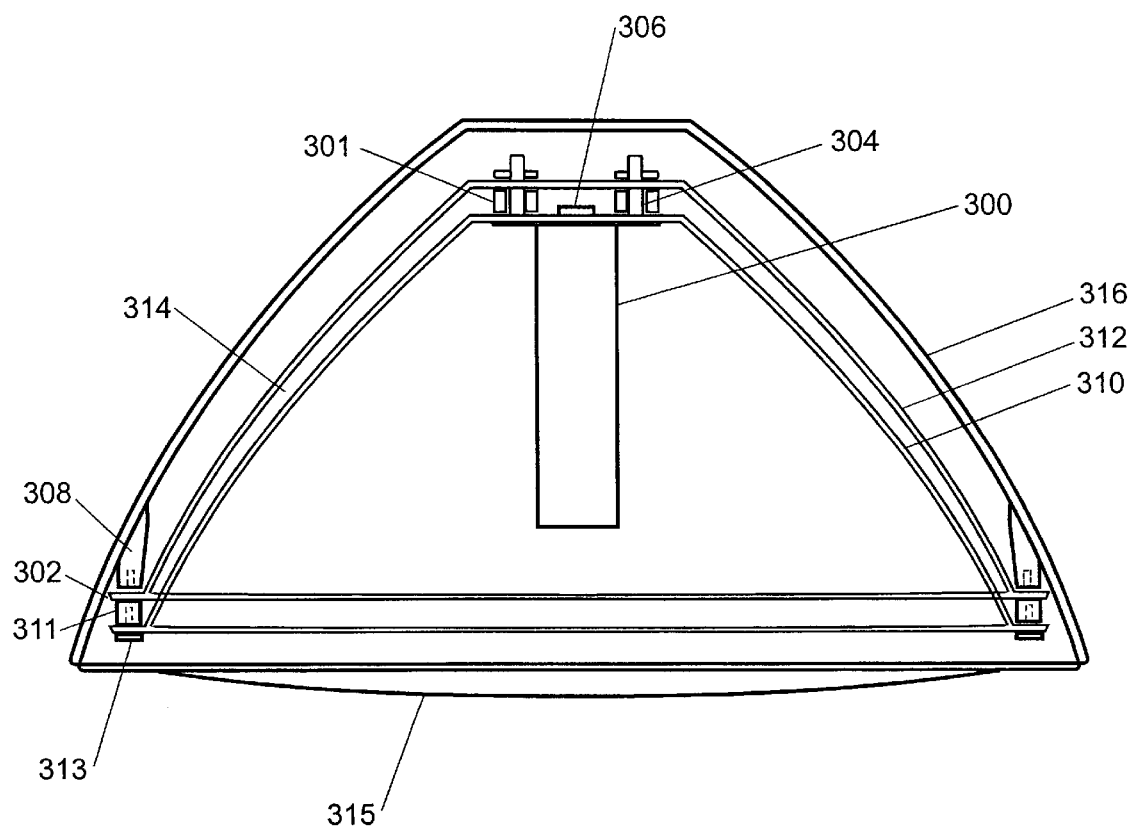
FIG. 3 is a cross-section view of the heater head according to the preferred embodiment of the present invention.

In the preferred embodiment of the present invention the warming head 111 is constructed using a double reflector design shown in more detail in FIG. 3. The double reflector has two purposes, firstly to minimise heat losses and secondly to ensure an acceptable outer temperature. The heater element 300 is attached by conventional fixing means 304 such as bolts, rivets etc to the inner reflector 310. Also provided are insulated terminals 306 which allow for electrical connection of the heater element 300 to the warmer controller 118.

Figure 4:
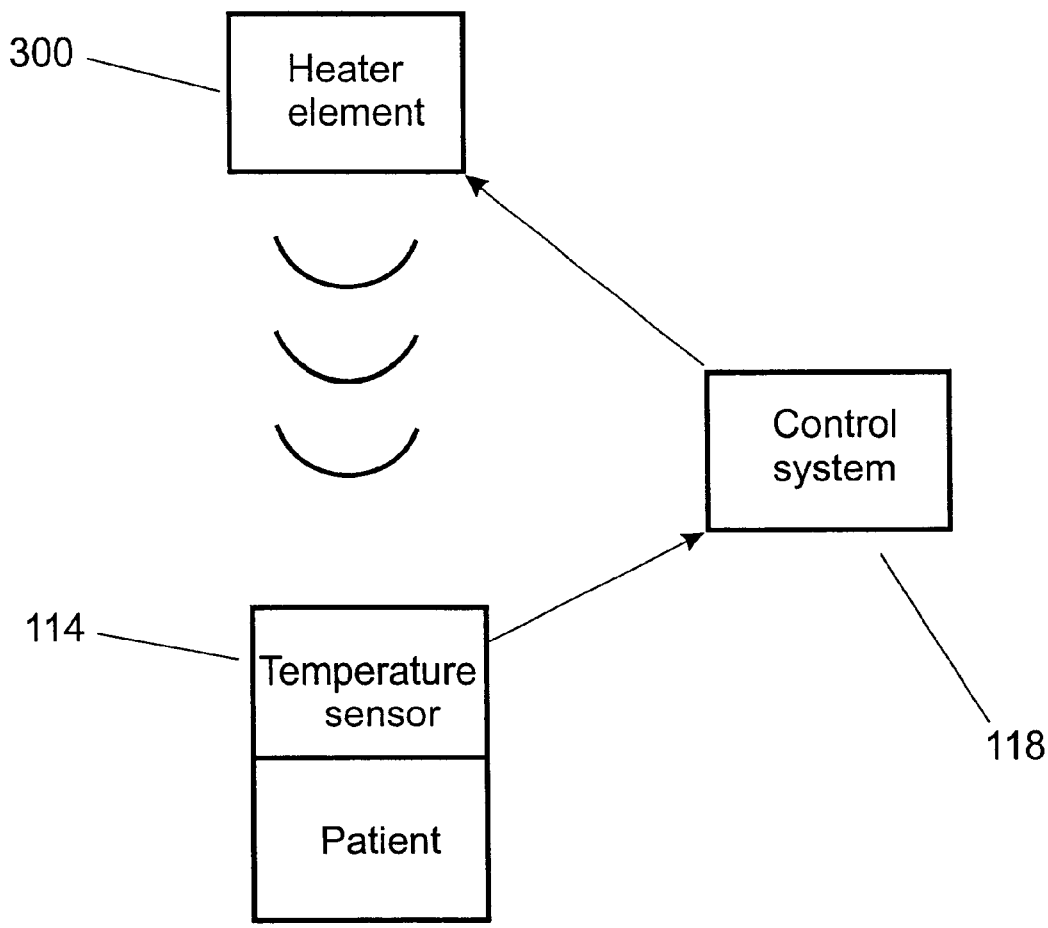
FIG. 4 is a block diagram of the control system according to the present invention.

Referring to FIG. 4 a system is illustrated for controlling the heater element 300. The heater element 300 is a solid cylindrical member which is typically heated to a maximum temperature of 680° C. which results in the ideal IR radiation of 3 micron wavelength. The heater element 300 is electrically connected to the warmer controller 118 which utilises closed loop control of the input desired skin temperature as compared against the measured skin temperature, using the temperature sensor 114.

In this fashion when the skin temperature is below the desired range, the heater element 300 is supplied with a voltage known to give the ideal wavelength of IR radiation at the controller 118. Once the skin temperature reaches the desired range the heater element 300 is switched off by the controller 118.

The inner reflector 310 through its attachment is in close thermal connection with the heater element 300. It is constructed using polished aluminium which has a high reflectivity but low emissivity for infrared radiation. The shape of the reflector resembles a parabolic shape and is specifically calculated to give a focussed beam of radiation of a width appropriate to heat areas such as the head, hands or feet. The exact shape (not strictly parabolic) can be easily calculated using anyone of a number of commercially available mathematical simulation packages run on a computer or any other method as is known in the art. To ensure users cannot get close to the heater element 300, a stainless steel mesh 315 is provided underneath to allow the radiation to pass, but stop any access.

An outer reflector 312, identical in shape and size to the inner reflector 310, is affixed at a small spacing from the inner reflector 310 at the top with the fixing means 304. It is also attached at the bottom 302 to the inner reflector 310 and the outer plastic casing 316. The outer casing 316 has a flange 308 on its inside on which the bottom 302 of the outer reflector 312 rests. A spacer 311 ensures the correct spacing, whereby further fixing means 313, for example, a screw or bolt, attaches through the reflectors 310, 312 into the flange 308 of the outer casing 316. This ensures the outer casing 316 is attached to the reflectors 310, 312 at their coolest point and therefore minimises any conduction losses. As the inner reflector 310 will be at a relatively high temperature some form of insulation is required on its outside to ensure that no energy is lost through any stray radiation or convection losses. While in the preferred embodiment the second reflector 312 is used it will be appreciated that any other methods as are known in the art could equally be used as, for example, "NOMEX" brand thermal insulation.

In the preferred embodiment of the present invention the air gap 314 created by the spacing between the outer reflector 312 and the inner reflector 310 provides the requisite insulation. In this fashion energy losses are minimised as well as allowing the temperature on the outside of the unit to be kept to acceptable levels. In this case the outer casing 316 is constructed using injection moulded plastics, and therefore cannot withstand high temperature. As the outer reflector may, for example, only reach 85° C. the outer casing 316 is able to be mounted relatively close to the outer reflector 312. It will be appreciated that in order to get a lower outer temperature more reflectors may be used, or NOMEX insulation may also be used between the two reflectors.

In order to minimise the footprint of the radiant heating unit, the unit 100 is secured by means of a bracket 122 at its base, to an adjacent structure. In the preferred embodiment of the present invention this bracket 122 is constructed such that it may attach to the rail 124 of any one of a number of designs of beds or surgical tables found in the hospital environment. By attaching the radiant heating unit 100 to the bed 126 as opposed to having a separate support structure, a significant amount of space is saved, the whole apparatus becomes less obtrusive and allows easy access to the patient. It will be appreciated however that the present invention might also be attached to any other nearby structures and need not necessarily be attached to the bed.

The present invention may be employed in one of two modes. Firstly, it may be used to initially raise the core temperature of a patient. In this case the skin temperature might be set using the interface with the controller 118 to range between 39° C. and 41° C. In this mode there will be a positive net energy transfer between the environment and the patient resulting in patient's core temperature rising. Once the patient's core temperature has reached an acceptable level the present invention may be employed in a second mode whereby it is used to maintain the core temperature of the patient. In this case the skin temperature might be set using the interface with the controller 118, for example at 37.5° C. which would result in a roughly zero net energy transfer between the patient and the environment. In this case the radiant warmer is only compensating for the heat losses of the patient.

It will be appreciated that in the normal course of surgery the initial skin temperature might be set quite high and then as the core temperature of the patient rises to that approaching the set skin temperature would be slowly titrated down to a maintenance level.

Case Studies: The three cases outlined below took place in confidential trials in Australia, in Perth, Melbourne and Brisbane respectively. All cases were done with the Fisher & Paykel PW810 Radiant Patient Warmer in a configuration substantially as described above.

Case 1 Thoracotomy:

The patient was in a right lateral position and the surgery was destined to be at least 3 hours. The patient was also an 80 year old lady who was likely to suffer significantly from heat loss.

The case started with the patient's core at 35° C. and the warmer was positioned with the warmer head shining almost exclusively over the patient's left cheek at a distance of around 40 cm, (we were working with such a small area that intensity was favoured rather than a larger surface area). The sensor was placed on the patient's cheek and a curtaining drape was placed in front of and over the head of the warmer to shield the surgeon. This also left no drape between the patient and the warmer itself.

This patient finished the procedure some four hours later with a core temperature of 36.2° C. and required no further warming. The surgeon was very happy as, despite being less than six inches away from the warmer head, he did not notice the heat at all due to the shielding drape. It seems we were able to transfer heat to the point of attaining a net heat gain with a surface area as small as just the left side of the head and neck. One thing was certain, prolonged maintenance of the head at a temperature of 39.5° C. appears to have no ill effects, with the patient being quickly recovered and comfortable, and the increased intensity was a fair trade off for loss of surface area.

Case 2 Colectomy, (Bowel Removal):

This case was on an eight year old Albanian child who was very emaciated, weighing in at only 20 kg. He had little or no body fat on him due to the fact that his bowel was very diseased and, in fact, was some seven times its normal size. The case was destined to be a long one and one that the anaesthetist was expecting the patient to be cold. In fact this case was extremely challenging, with the child having wild swings in both skin and core temperature depending on how much bowel was exposed or even what the air conditioning was doing.

The warmer was positioned above the patient's head/neck area at a distance of around 40 cm. The height was chosen as a balance, between narrowing the field out of the surgeon's way and intensity. The sensor was initially positioned on the cheek, (his head was turned to the side), as this was the most prominent point with two layers of cotton draping over the face and head. On starting his core temp was 35.1° C. but continued to rise until we had established a core temp of 36.7° C. and the skin temp was dialled back to 37.5° C. to maintain rather than pump heat in. His core and skin temp remained constant and at the conclusion of the procedure, (some seven hours), was 37.0° C. The anaesthetist was impressed with the controllability of the warmer, as we could see an instant response in warming rate as we changed the set temp. She also found the unit efficient in terms of core rewarming, stating that she wouldn't have expected normal treatment, (convective air warming), to have achieved this result.

Case 3 Open Reduction of Humorous With Tendon Transfer and Bone Graft:

This case was set to be at least 6 hours with involvement from both orthopaedic and plastics teams. The theatre, therefore, was cluttered with both two lots of staff and extra equipment, including an Image Intensifier machine over the upper right arm and shoulder. The patient himself was obese and had a large surface area for heat transfer but we would be unable to heat anywhere below the neck area as he would be surgically prepared from the shoulders down to mid-thigh, as the bone graft was being taken from the left hip. From mid-thigh to ankle, because of his weight, he had devices fitted to his legs to help maintain his circulation and prevent clots forming through this long case. As a result we positioned the Patient Warmer over just the head and neck area, at a distance of 40 cm with the sensor on the forehead and a set temperature of 39.5° C.

We started the case with a core temp of 35.8° C. and over the first 15 minutes brought core up to 36.2° C. It was at this point that the theatre temp was dropped by 6° C. for comfort because the staff were wearing several layers of gown, including lead aprons. The result halted the core rise but we maintained at this level for the next four hours or so. Once the bone graft was finished, the patient was redraped and the room temp turned up 3° C. which initiated the core rewarming again. The last two hours was spent at 36.9° C. with the set skin temp lowered to 37.5° C. as pure maintenance. Total operating time was 7 hours with the final core temp recorded as 37° C. and no adverse effects from the positioning. In terms of this unit, this patient was a test case. The anaesthetic staff were impressed with the results. The anaesthetist expressed a desire to see the warmer trialed on liver transplant cases as they find it impossible to warm with convective air warmers. It fitted in well with surgical team and interacted with image intensifier well utilizing the space above the head which is frequently the only available space in a surgical procedure.

These three cases outline the effect of heating the head/neck region of the patient during a surgical procedure. It also shows a cross-section of cases where this technique can be utilized. This technique should prove successful in many more surgical procedures not involving neurosurgery.

We believe that the technique exploits the properties of one of several specialized areas which it utilizes for thermoregulation. These are the face/neck, ears, hands and feet. A few millimetres below the surface of the skin in these areas lies the Arteriovenous plexus. The Arteriovenous plexus is a layer of blood vessels which contain Arteriovenous Anastomoses, (AVA), which, when dilated, shunt blood directly from the arterial to the venous system bypassing the capillary beds. This allows the body to shunt a great deal of blood in order to lose heat if the core temperature rises. However, it appears to also allow free access of heat directly into the core circulation if external heat is being applied.

We believe that the present invention exploits this portal by raising the temperature of the skin in the head/neck area quickly thereby causing a dilation of the AVA allowing heat energy to be transferred directly into the core circulation. The controller allows the unit to maintain a high energy intensity whilst controlling the patient's skin at a safe level.

It will also be appreciated that such a method is not limited specifically to humans and is generally applicable for use with animals generally, although particularly with warm blooded mammals.

We believe that this method of heating is unique to the radiant warmer and cannot be achieved by the current warming technique of choice which is convective air warming. This is due to several reasons:

1. To achieve the necessary vasodilation and consequent dilation of the AVA, a high energy source is needed to raise the skin temperature significantly.

2. To maintain this skin temperature necessary for vasodilation, without risk of overheating causing injury, some form of patient feedback mechanism is required together with accurate and effective response. The present invention uses a controller and skin sensor to monitor skin temperature and adjust the unit's heat output. The radiant nature of the warmer gives near instantaneous control of heat output to the patient. This allows the Radiant system to achieve and maintain the desired skin temperature safely.

Convective air warmers do not have a patient feedback system and so have no way of controlling skin temperature. By default, therefore, they achieve a much lower skin temperature as, without control, they run a risk of causing thermal injury to the patient.

3. In the preferred embodiment of the present invention the patient is radiated with IR at a peak wavelength of 3 microns. We believe that this wavelength achieves a penetration through the skin of approximately 1–2 mm, allowing energy to be transferred directly into the tissue. This raises the temperature of the tissue quickly, rapidly establishing the desired vasodilation of the AVA, and allows transfer of heat energy directly into the circulation. Convective air warmers however, pass their energy through the skin's surface via conduction slowing the transfer of the energy into the deeper tissues and the circulatory system, and limiting the safe transfer rate.

Alternative Embodiments

Figure 2:
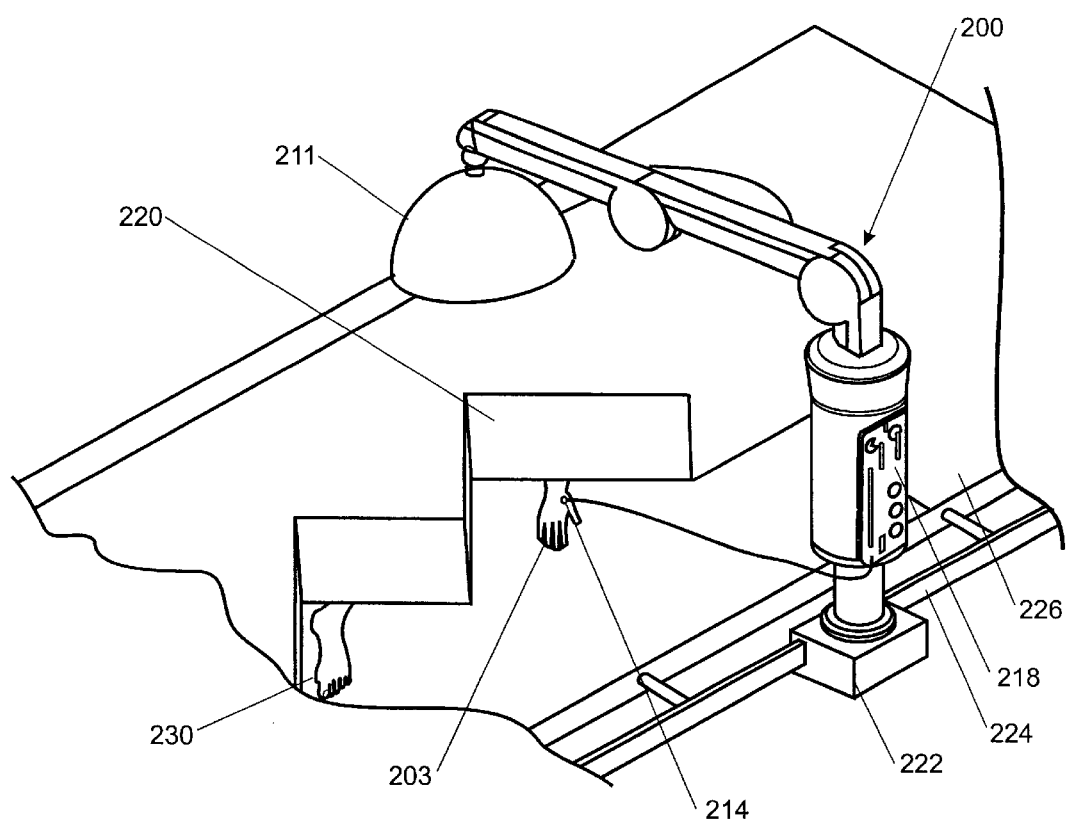
FIG. 2 is a block diagram of the present invention in use heating the hand region.

As previously described as well as the head/neck area, the hands (and also feet) also have a concentration of AVA. Thus the method previously described might be applied in a similar fashion as shown in FIG. 2 to warm the hand area. This would be of use for example in neurosurgery where the head is not available for heating.

In the preferred embodiment of the present invention seen in FIG. 2, the unit 200 is positioned over one of the patient's hands 203. With only a small surface area to work with, the distance between the warmer 211 and the patient's hand 203 is 20–50 cm, to ensure effective intensity of the IR. A skin sensor 214 is positioned on a prominent point on the patient's hand 203. A surgical drape 220 may be used to shield the surgical team from any stray radiation. As with the preferred embodiment the radiant heating unit 200 is secured by a bracket 222 to the rail 224 of a hospital bed 226. As already mentioned a further alternative would be to heat one foot 230 of the patient.

Case Studies: The two cases outlined below took place in confidential trials in New Zealand at Middlemore Hospital.

Case 4 Ear Tuck Repair

The patient was a 10 year old male. In this operation our normal preferred warming site, the head, was unavailable due to the nature of the operation. Knowing the hand has a large number of AVA suitable for energy transfer I set the heater unit over the right hand/wrist area which was supported by an arm support extension. The set temperature was 41° C. and the skin sensor attached to the base of the thumb, being the portion of the hand closest to the heater.

The patient's core temperature was monitored using a naso-pharyngeal probe with a start core temperature of 37° C. At 30 mins the core temperature was 36.6° C. The warmer was removed 5 minutes later at the end of the operation.

Upon admission to recovery ward the patient was found to have a 36.7° C. left axilla temperature, much higher than expected. The normal discharge temperature is 35.5° C. axilla. Nurses commented on the warm condition of the patient.

Case 5 Tonsillectomy

The patient was a 41 year old female. Again an operation which precluded warming of the head. The heater was positioned over the right hand/wrist area and set at 41° C. The sensor again placed on the base of the thumb. Core temperature was measured using a Braun Thermoscan tympanic sensor at 20 mins the core measured 37.5° C. the warmer was removed 5 minutes later, in recovery ward the patient's left axilla temperature was measured to be 36.6° C. Again an unusually high recovery admission temperature.

Thus it will be appreciated that what is described is an effective method and apparatus of heating a patient during surgery. In the preferred embodiment the head/neck area is heated, however other areas such as the hands or feet which have high AVA concentration, may also be used. The apparatus allows excellent regulation of the patient's core temperature throughout surgery and is unobtrusive allowing good access for the surgical team.

What we claim is:

1. An apparatus for raising or maintaining the core temperature of a mammal comprising:

radiant heating means which in use are located in an unobtrusive position proximate to said mammal, said radiant heating means comprises a cylindrical heating element which radiates heat energy with a wavelength of 3 microns when heated to 680° C.;

means adapted to direct radiant energy produced by said radiant heating means at said mammal substantially at a region of high concentration of Arteriovenous Anastomoses, said energy being radiated using a wavelength of approximately 3 microns in the infrared band, said means adapted to direct radiant energy comprising two radiant energy reflectors, a first reflector being mounted directly or indirectly to said heating element, said heating element thereby being on the forward side of said first reflector, and said insulating means comprising a second reflector being mounted directly or indirectly to said first reflector a small distance from and on the behind side thereof, each said radiant energy reflector being shaped to direct said radiant energy from said radiant heating means in a substantially narrow beam, said beam being of a width substantially approximating said region, and insulating means for minimizing radiant and convection energy loss from said radiant means; and control means adapted to energise said radiant heating means such that in use the skin temperature of said mammal substantially adjacent said region remains within a predetermined range.

2. An apparatus for raising or maintaining the core temperature of a mammal comprising:

radiant heating means which in use are located in an unobtrusive position proximate to said mammal, said radiant heating means comprises a cylindrical heating element which radiates heat energy with a wavelength of 3 microns when heated to 680° C.;

means adapted to direct radiant energy produced by said radiant heating means at said mammal substantially at a region of high concentration of Arteriovenous Anastomoses, said energy is radiated using a wavelength in the infrared band, said wavelength being approximately 3 microns, said means adapted to direct radiant energy comprises two radiant energy reflectors shaped to direct said radiant energy from said radiant heating means in a substantially narrow beam, said beam being of a width substantially approximating said region, a first reflector being mounted directly or indirectly to said heating element, said heating element thereby being on the forward side of said first reflector, and a second reflector being mounted directly or indirectly to said first reflector a small distance from and on the behind side thereof, and control means adapted to energise said radiant heating means such that in use the skin temperature of said mammal substantially adjacent said region remains within a predetermined range.

3. A method of raising or maintaining the core temperature of a mammal using a radiant heater comprising the steps of:

1) positioning the radiant heater in a non-obtrusive manner in proximity to said mammal;

2) energising said radiant heater;

3) directing the radiant energy produced in step (2) at said mammal substantially at a region of high concentration of Arteriovenous Anastomoses; and 4) controlling the energisation of said radiant heater such that the skin temperature of said mammal substantially adjacent said region remains within a predetermined range.

4. A method as claimed in claim 3 wherein said radiant energy is directed specifically at a region of the head or neck of said mammal.

5. A method as claimed in claim 3 wherein said radiant energy is directed specifically at a region of a hand (or front leg) of said mammal.

6. A method as claimed in claim 3 wherein said radiant energy is directed specifically at a region of a foot of said mammal.

7. A method as claimed in claim 3 wherein said energy is radiated using a wavelength in the infrared band.

8. A method as claimed in claim 7 wherein said wavelength is approximately 3 microns.

9. A method as claimed in claim 3 wherein said radiant heater is positioned approximately 20–50 cm from said mammal.

10. A method as claimed in claim 3 wherein when raising the core temperature of said mammal the said predetermined range of said mammal's skin temperature is approximately of 39° C. to 41° C.

11. A method as claimed in claim 3 wherein when maintaining the core temperature of said mammal the said predetermined range lies about a skin temperature of 37.5° C.

12. A method as claimed in claim 3 wherein said method includes an initial step of positioning a temperature sensor on said mammal's skin in proximity to said region, including monitoring the output of said temperature sensor to indicate said mammal's skin temperature in said region.

13. A method as claimed in claim 3 wherein said mammal is positioned on a support structure onto which said radiant heater is attached.

14. A method as claimed in claim 13 wherein said support structure is a hospital bed or operating table including surrounding rails and said radiant heater is attached to and supported by said rails.

* * * * *